United States Patent [19]

Shuler

[11] Patent Number: 5,061,238
[45] Date of Patent: * Oct. 29, 1991

[54] SURGICAL CUTTING INSTRUMENT WITH TITANIUM NITRIDE COATING ON AN INNER TUBULAR MEMBER

[75] Inventor: Donald K. Shuler, Largo, Fla.

[73] Assignee: Linvatec Corporation, Largo, Fla.

[*] Notice: The portion of the term of this patent subsequent to May 8, 2007 has been disclaimed.

[21] Appl. No.: 513,291

[22] Filed: Apr. 25, 1990

Related U.S. Application Data

[63] Continuation-in-part of Ser. No. 311,196, Feb. 23, 1989, Pat. No. 4,923,441.

[51] Int. Cl.$^5$ ............................................. A61B 17/32
[52] U.S. Cl. ......................................... 604/22; 606/170
[58] Field of Search ...................... 606/168, 170, 171; 604/22; 128/750, 751, 752; 384/280, 317, 476, 900, 912, 913; 408/144; 427/190

[56] References Cited

U.S. PATENT DOCUMENTS

| | | | |
|---|---|---|---|
| 4,203,444 | 5/1980 | Bonnell et al. | 604/22 |
| 4,819,635 | 4/1989 | Shapiro | 604/22 |
| 4,923,441 | 5/1990 | Shuler | 604/22 |

Primary Examiner—C. Fred Rosenbaum
Assistant Examiner—William W. Lewis
Attorney, Agent, or Firm—Epstein, Edell & Retzer

[57] ABSTRACT

A surgical cutting instrument having elongate inner and outer tubular members with distal ends cooperating to cut bodily tissue and aspirate the cut bodily tissue through the inner tubular member includes a coating of titanium nitride formed on the inner tubular member to extend from the distal end to the proximal end thereof such that the titanium nitride coating forms an elongate bearing surface extending along the length of the surgical cutting instrument to prevent cocking or skewing of the inner tubular member relative to the outer tubular member, to increase the surface hardness of the inner tubular member, to reduce the coefficient of friction of the inner tubular member and to prevent galling and possible seizure of the inner tubular member by distributing or dispersing heat along the surgical cutting instrument while reducing the clearance between the outer diameter of the inner tubular member and the inner diameter of the outer tubular member.

26 Claims, 1 Drawing Sheet

FIG. 1

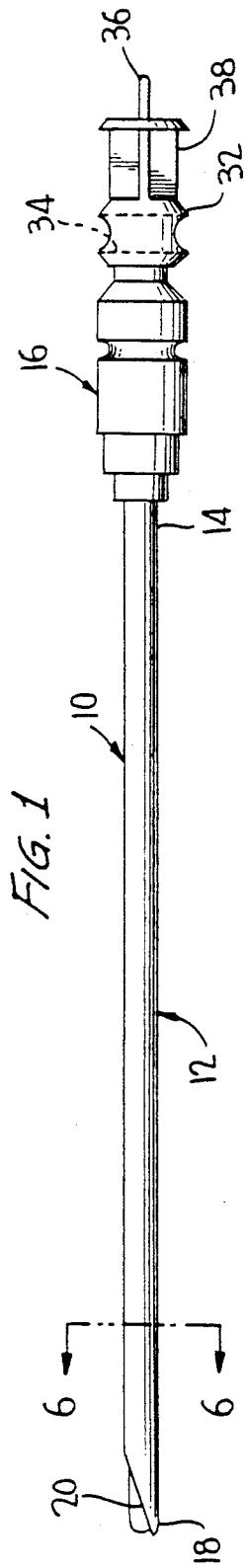
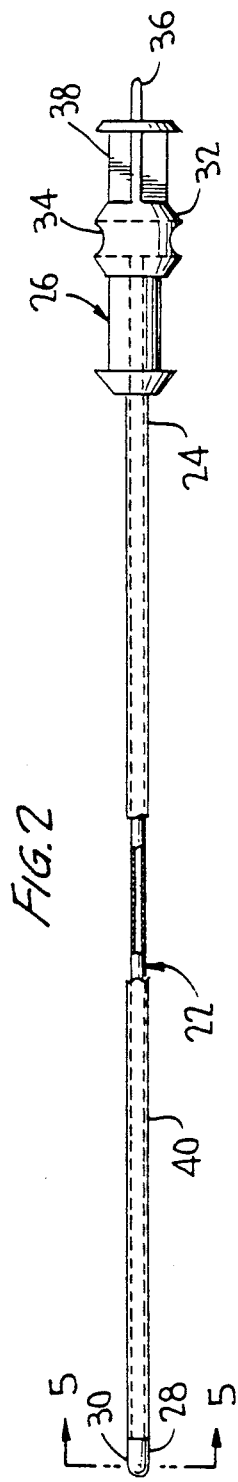
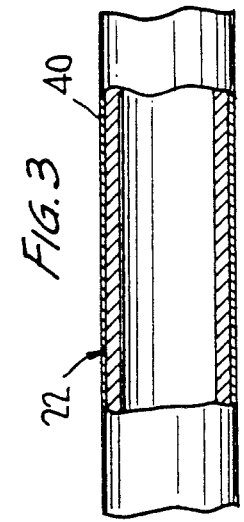
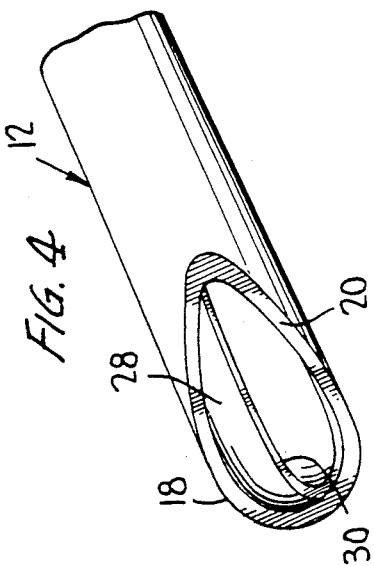
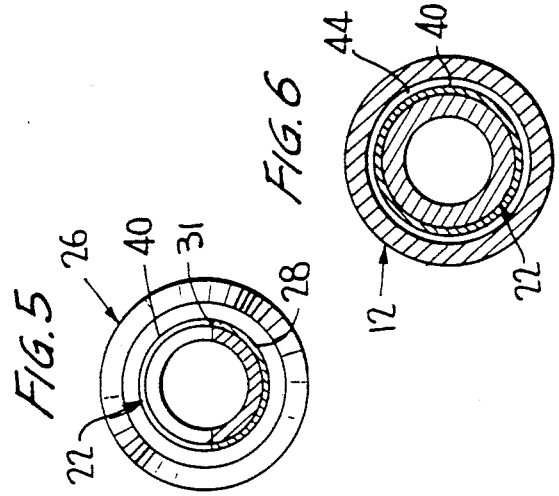
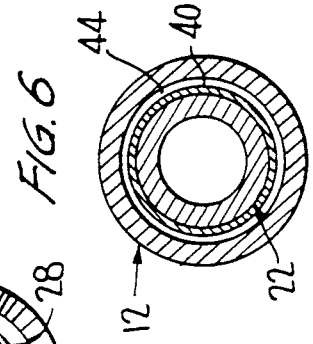

SURGICAL CUTTING INSTRUMENT WITH TITANIUM NITRIDE COATING ON AN INNER TUBULAR MEMBER

This application is a continuation-in-part of application Ser. No. 07/314,196 filed Feb. 23, 1989 now U.S. Pat. No. 4,923,441.

BACKGROUND OF THE INVENTION

1. Field of the Invention

The present invention pertains to surgical cutting instruments and, more particularly, to surgical cutting instruments having elongate inner and outer tubular members with distal ends cooperating to cut or resect bodily tissue, the cut tissue being aspirated through the inner member.

2. Discussion of the Prior Art

The use of elongate surgical cutting instruments has become well accepted in performing closed surgery, such as arthroscopic or, more generally, endoscopic surgery. In closed surgery, access to the surgical site is gained via one or more portals, and instruments used in the surgical procedure must be elongated to permit the distal ends of the instruments to reach the surgical site. Surgical cutting instruments for use in closed surgery conventionally have an elongate outer tubular member terminating at a distal end having an opening in the side wall, the end wall or both to form a cutting port or window and an elongate inner tubular member concentrically disposed in the outer tubular member and having a distal end disposed adjacent the opening in the distal end of the outer tubular member. The distal end of the inner tubular member has a surface or edge for engaging tissue via the opening in the distal end of the outer tubular member and in many cases cooperates with the opening to shear or cut tissue. The inner tubular member is rotatably driven at its proximal end, normally via a handpiece having a small electric motor therein controlled by finger-actuated switches on the handpiece, a foot switch or switches on a console supplying power to the handpiece. The distal end of the inner tubular member can have various configurations dependent upon the surgical procedure to be performed, and the opening in the distal end of the outer tubular member has a configuration to cooperate with the particular configuration of the distal end of the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to generically as "cutting blades or edges". Cut tissue is aspirated through the hollow lumen of the inner tubular member to be collected via a tube communicating with the handpiece.

It is very important in such surgical cutting instruments that the cutting edge be precisely positioned and aligned relative to the opening in the distal end of the outer tubular member. Accordingly, a bearing structure must be provided to obtain precise positioning and alignment of the cutting edge while permitting unrestricted rotation of the inner tubular member within the outer tubular member. That is, the inner tubular member cannot be allowed to cock or be positioned askew of the longitudinal axis of the surgical cutting instrument as a reaction to the cutting action. This problem has been difficult to overcome in the past. The addition of bearing surfaces at the distal end of the surgical cutting instrument or at spaced positions along the surgical cutting instrument requires complex structure and manufacturing techniques and results in a relatively expensive product that cannot be feasibly supplied for single patient use, i.e., be disposable. Additionally, such bearing structures present increased opportunities for malfunction due to sticking and obstruction.

Another manner in which to precisely position and align the inner member is to make the outer diameter of the inner member substantially the same as the inner diameter of the outer tubular member, or as close as possible thereto, so that there is little or virtually no gap or clearance between the inner tubular member and the outer tubular member. However, it is preferred to construct the inner tubular member and the outer tubular member of stainless steel, and the physical properties of stainless steel limit its effectiveness as a rotational bearing surface. In particular, stainless steel is relatively soft, having a surface hardness of 30–35 Rc, and possesses a high coefficient of friction. Moreover, the inner and outer stainless steel tubular members are subjected to considerable thrust and radial loads during operation wherein the inner tubular member can rotate at speeds greater than 2,500 RPM. If the stainless steel surfaces of the inner and outer tubular members bear on and contact each other, such as occurs when the clearance between the inner and outer member is small, heat will be generated from friction and cause thermal expansion of the inner tubular member. As the area of contact between the inner tubular member and the outer tubular member increases, greater friction will be created with a concomitant increase in heat eventually causing the grain structure of the stainless steel tubular members to "flake", in turn increasing temperature due to abrasion until the inner tubular member has expanded further than the gap between it and the outer tubular member and the instrument seizes. No adequate solution to this problem has been found prior to the present invention, it being noted that biocombatibility must be considered in using a lubricant coating between the inner and outer members. Thus, prior art efforts have sacrificed optimum cutting quality for prolonged life of the cutting instrument by increasing the clearance between the inner tubular member and the outer tubular member. A typical range for the clearance maintained between the inner tubular member and the outer tubular member of a surgical cutting instrument ranges from a minimum of 0.00115 inches to a maximum of 0.00285 inches. The clearance associated with conventional surgical cutting instruments results in reduced cutting efficiency, and there is a need to produce precision cutting with such instruments to allow their use in various different surgical procedures.

Titanium nitride (TiN) has been used on cutting tools for industrial applications to provide the benefits of longer life and higher productivity as described, for example, in various literature and brochures from Balzers Tool Coatings, Inc. TiN coatings are applied by placing physically and chemically clean tools in fixtures to become the cathode of a high voltage circuit in a reaction chamber that is evacuated and charged with argon. By sputter cleaning, positive argon ions are propelled by a high voltage field and blast the tool to make the tool atomically clean. An electron beam gun heats titanium until the titanium evaporates. Nitrogen is introduced into the chamber, and the titanium ions are electrically accelerated toward the tools. The titanium ion bombardment combines with the nitrogen gas to form a coating of TiN about 0.0001 inch thick on the surface of the tool. The coating process is called "physical vapor deposition" and operates at temperatures in the 900° F. range.

In the past, cutting tools have been coated at the cutting edges thereof with TiN by physical vapor deposition for the purpose of hardening the cutting edge thereby providing the cutting tool with an extended useful life; however, there has been no recognition of the use of TiN coatings by physical vapor deposition to limit heat conduction along a rotating tubular member to produce a bearing structure for inner and outer members made of stainless steel.

A further consideration affecting the performance of a cutting instrument including an inner tubular member movably mounted within an outer tubular member relates to the cutting aperture configuration. As previously noted, any number of configurations may be formed in the distal end of the inner tubular member depending upon the surgical procedure to be performed, and the window or port in the distal end of the outer tubular member is configured to cooperate with the particular configuration of the distal end of the inner tubular member. The interface between the stationary outer tubular member and the movable inner tubular member governs the sharpness of the cut and the efficiency of the cut as determined by the closing force required to complete the cut. Traditionally, the cutting surface or edge in the distal end of the inner tubular member is formed by cutting away a portion of the inner tubular member above its center line. The resulting cutting edge or surface lies above the center line of the inner tubular member and thus includes a relatively dull obtuse angle on the outside diameter of the inner tubular member requiring significant closing force to move the cutting edge past the cutting port or window in the distal end of the outer tubular member when shearing tissue.

SUMMARY OF THE INVENTION

Accordingly, it is a primary object of the present invention to overcome the above mentioned problems and disadvantages associated with surgical cutting instruments formed of relatively movable, elongate, inner and outer tubular members.

Another object of the present invention is to provide an elongate bearing structure for a surgical cutting instrument having elongate inner and outer tubular members to prevent cocking or skewing of the inner member relative to the outer member without creating galling and possible seizure during operation of the surgical cutting instrument.

It is a further object of the present invention to minimize the clearance between the inner and outer tubular members of a surgical cutting instrument to achieve greater cutting efficiency and to enable the cutting instrument to cut with great precision.

Another object of the present invention is to increase the surface hardness and minimize the coefficient of friction of the inner tubular member of a surgical cutting instrument.

A further object of the present invention is to disperse or distribute heat along the length of a surgical cutting instrument during operation to avoid hot spots and prevent concentration of heat at the cutting edge at the distal end of the surgical cutting instrument.

The present invention has another object in that stainless steel inner and outer tubular members can be used in an elongate surgical cutting instrument without galling or seizure.

An additional object of the present invention is to provide a gap of approximately 0.00075 inches or less between inner and outer tubular members of a surgical cutting instrument to obtain greater cutting efficiency.

A further object of the present invention is to provide a relatively sharp acute cutting angle on the cutting edge of an inner tubular member movably mounted in an outer tubular member in a surgical cutting instrument.

Some of the advantages of the present invention over the prior art are that the surgical cutting instrument of the present invention can be economically manufactured for single patient use since precise bearing support is provided without expensive and complex structural modifications and without subjecting the surgical cutting instrument to galling or seizure during operation, and the surgical cutting instrument can be manufactured with only a single added process step.

The present invention is generally characterized in a surgical cutting instrument having an elongate outer tubular member having a proximal end, a distal end and an opening disposed at the distal end, an elongate inner tubular member having a proximal end, a distal end and a cutting edge disposed at the distal end, the inner tubular member being movably received in the outer tubular member to position the proximal end of the inner tubular member adjacent the proximal end of the outer tubular member, the distal end of the inner tubular member adjacent the distal end of the outer tubular member and the cutting edge adjacent the opening to permit the cutting edge to engage bodily tissue through the opening, and a coating of titanium nitride formed on the inner tubular member extending from the distal end to the proximal end thereof, the inner tubular member having an outer diameter substantially the same as or as close as possible to the inner diameter of the outer tubular member such that the gap or clearance between the inner tubular member and the outer tubular member is approximately 0.00075 inches or less and the titanium nitride coating forms an elongate bearing surface having a surface hardness of approximately 80 Rc or more and a coefficient of friction of approximately 0.5 or less extending along the length of the surgical cutting instrument.

Other objects and advantages of the present invention will become apparent from the following description of the preferred embodiment taken in conjunction with the accompanying drawings.

BRIEF DESCRIPTION OF THE DRAWINGS

FIG. 1 is a side elevation of a surgical cutting instrument according to the present invention.

FIG. 2 is a side elevation, partially broken away, of an inner tubular member of the surgical cutting instrument of FIG. 1.

FIG. 3 is an enlarged broken section of the inner tubular member.

FIG. 4 is an enlarged perspective view of the distal end of the surgical cutting instrument of the present invention.

FIG. 5 is an enlarged cross-sectional view of the inner tubular member taken along line 5—5 in FIG. 2.

FIG. 6 is an enlarged cross-sectional view of the surgical cutting instrument taken along line 6—6 of FIG. 1.

DESCRIPTION OF THE PREFERRED EMBODIMENT

A surgical cutting instrument 10 according to the present invention is illustrated in FIG. 1 and includes an elongate tubular outer member 12 made of stainless steel and having a proximal end 14 fixed to a plastic hub 16 and a distal end 18 having an opening 20 therein forming a cutting port or window. An elongate tubular inner member 22 made of stainless steel is rotatably received in outer tubular member 12 and, as shown in FIG. 2, has a proximal end 24 fixed to a plastic hub 26 having a configuration to be received in a recess (not shown) in hub 16 and a distal end 28 having a cutting edge 30 formed thereon and positioned adjacent opening 20 such that the cutting edge can engage bodily tissue. The hub 26 has a central portion 32 with a transversely extending passage 34 therethrough, the inner tubular member extending through an axial bore in hub 26 to communicate with passage 34. A driven tang 36 extends from a portion 38 formed of transverse ribs and is adapted to be driven by a rotating slotted drive shaft of an electric motor in a handpiece. The structure of hubs 16 and 26 is described in brief general terms only since the hubs are the same as utilized on the INTRA ARC cutting blades manufactured by Concept Incorporated and designed for use with the INTRA ARC Model 9930 arthroscopic drive system of Concept Incorporated and the Model 9950H handpiece thereof.

The opening 20 in the distal end of the outer tubular member 12 extends through the side and end walls to produce an edge cooperating with the cutting edge 30 formed on the distal end 28 of the inner tubular member 22 to form a full radius resector. As shown in FIG. 5, the cutting edge 30 is preferably formed by cutting away a portion of the distal end 28 of the inner tubular member 22 below the center line of the inner tubular member to define an acute angle at the outermost diametrical edge 31. The acute angle at edge 31 presents a sharp or steep cutting surface to reduce the force required in rotating the inner tubular member to move the cutting edge 30 past the opening 20 in the distal end of the outer tubular member to cut tissue. The opening 20 can have any desired configuration to cooperate with the configuration of the cutting edge or edges on the distal end of the inner tubular member including, but not limited to, the various cutting tip designs of the Concept INTRA ARC Blade System, such as to form trimmers, meniscus cutters, end cutters, side cutters, full radius resectors, synovial resectors, whiskers, open end cutters, arthroplasty burrs, slotted whiskers, tapered burrs, oval burrs and punch forceps. While the surgical cutting instrument of the present invention is shown and described for use in the Concept INTRA ARC system, it will be appreciated that the surgical cutting instrument of the present invention can have any desirable hub configuration to be utilized with any drive system or handpiece capable of rotating an elongate inner tubular member within an elongate outer tubular member to cut or otherwise engage bodily tissue at the distal end and aspirate cut tissue through the lumen of the inner tubular member.

In accordance with the present invention, the inner tubular member 22 has a titanium nitride (TiN) coating 40 formed thereon by physical vapor deposition, the coating 40 being disposed along substantially the full length of the inner tubular member from the distal end 28, including the cutting edge 30, to the proximal end 24. It is preferable to coat the entire length of the inner tubular member such that the coating 40 extends under the distal end of the hub 26. The coating of TiN 40 has a 0.0001 inch such that the outer diameter of inner tubular member 22 can be substantially the same as the inner diameter of outer tubular member 12 creating a minimum gap or clearance 44, shown in exaggerated form in FIG. 6, between the inner tubular member and the outer tubular member is very small. A clearance of approximately 0.00075 inches produces excellent precision cutting and, preferably, the clearance is 0.00050. With the use of the TiN coating, the 0.0050 clearance, as well as the 0.00075 clearance, can be obtained without creating galling or seizing during operation. The coating 40 along the outer surface of the inner tubular member forms a bearing surface along the length of the surgical cutting instrument for engaging the inner surface of the outer tubular member as the inner member moves with respect to the outer member. By using the TiN coating to form a bearing along the length of the inner tubular member, rather than only on the distal end and cutting edges which engage the bodily tissue, unexpectedly a surgical cutting instrument is provided in an economically feasible manner for single patient use (disposable) while still providing precision positioning of the inner tubular member within the outer tubular member and while using stainless steel inner and outer tubular members. The TiN coating 40 is shown of exaggerated thickness in FIGS. 2 and 3 since the coating is so thin that it cannot be illustrated if the figures are to scale. The TiN coating provides the stainless steel inner tubular member with a surface hardness having a value of approximately 80 Rc and greater, as opposed to a surface hardness of 30 to 35 Rc for uncoated stainless steel. Furthermore, the TiN coating increases the effectiveness of the stainless steel inner tubular member as a bearing surface by reducing the coefficient of friction for the outer surface of the inner tubular member to approximately 0.5 or less.

In operation, the inner tubular member is rotatably driven in the outer tubular member such that the cutting edge 30 engages bodily tissue via the cutting port or window formed by opening 20, and the cut tissue is aspirated through the lumen of the inner tubular member to exit the surgical cutting instrument via passage 34 which communicates with a suction passage at the handpiece. The cutting edge 30 will be maintained in precise position at the opening 20 due to the bearing formed by the TiN coating along the length of the surgical cutting instrument, and the considerable thrust and radial loads placed on the inner and outer tubular members will not cause galling due to the uniform distribution of heat along the length of the bearing surface created by the TiN coating. In this manner, hot spots are avoided, and the heat distribution or dispersion along the length of the surgical cutting instrument prohibits concentration of heat at the cutting tip as would occur with no coating or coating only at the cutting tip. Accordingly, easier and smoother cutting is accomplished with the surgical cutting instrument of the present invention, and precision cutting can be accomplished while preventing tissue from entering the gap and wrapping around the inner tubular member. Moreover, the acute angle provided on the outer diameter of the inner tubular member at the cutting edge presents a relatively sharp edge for penetrating and shearing through tissue projecting through the window in the outer tubular member. Thus, less force is required to move the cutting edge through the tissue and past the window in the outer member than would be required if the cutting edge were an obtuse angle as would be obtained if the cutting edge was formed in the inner member above the center line or longitudinal axis.

Inasmuch as the present invention is subject to many variations, modifications and changes in detail, it is intended that the subject matter discussed above and shown in the accompanying drawings be interpreted as illustrative and not in a limiting sense.

What is claimed is:

1. A surgical cutting instrument comprising
   an elongate outer tubular member having a distal end and an opening disposed at said distal end;
   an elongate inner tubular member having a distal end and a cutting edge disposed at said distal end, said inner tubular member being movably received in said outer tubular member to position said distal end of said inner tubular member adjacent said distal end of said outer tubular member and said cutting edge adjacent said opening to permit said cutting edge to engage bodily tissue through said opening; and
   a coating of titanium nitride formed on said inner tubular member and said cutting edge to form an elongate bearing surface along the length of said inner tubular member, said inner tubular member having an outer diameter substantially the same as the inner diameter of said outer tubular member such that the clearance between the outer diameter of said inner tubular member and the inner diameter of said outer tubular member is approximately 0.0075 inches or less.

2. A surgical cutting instrument as recited in claim 1 wherein said titanium nitride coating has a thickness of substantially 0.0001 inch.

3. A surgical cutting instrument as recited in claim 2 wherein said outer tubular member and said inner tubular member are each made of stainless steel.

4. A surgical cutting instrument as recited in claim 3 wherein said outer tubular member includes a proximal end with a plastic hub fixed thereto and said inner tubular member includes a proximal end with a plastic hub fixed thereto and having a portion received in said hub of said outer tubular member and a portion having a passage extending therethrough in communication with the lumen of said inner tubular member for aspiration of cut bodily tissue.

5. A surgical cutting instrument as recited in claim 1 wherein the outer surface of said inner tubular member has a surface hardness of approximately 80 Rc and greater.

6. A surgical cutting instrument as recited in claim 1 wherein the outer surface of said inner tubular member has a coefficient of friction of approximately 0.5 or less.

7. A surgical cutting instrument as recited in claim 1 wherein said inner tubular member is rotatably received in said outer tubular member.

8. A surgical cutting instrument as recited in claim 7 wherein said outer tubular member and said inner tubular member are each made of stainless steel and said outer tubular member includes a proximal end with a plastic hub fixed thereto and said inner tubular member includes a proximal end with a plastic hub fixed thereto over said coating and having a portion received in said hub of said outer tubular member and a portion having a passage extending therethrough in communication with the lumen of said inner tubular member for aspiration of cut bodily tissue.

9. A surgical cutting instrument as recited in claim 1 wherein said cutting edge is disposed below the longitudinal center line of said inner tubular member.

10. A surgical cutting instrument as recited in claim 9 wherein said cutting edge defines an acute angle at the outer diameter of said inner tubular member.

11. A surgical cutting instrument comprising
    an elongate outer tubular member having a distal end and an opening disposed at said distal end;
    an elongate outer tubular member having a distal end and a cutting edge disposed at said distal end, said inner tubular member being movably received in said outer tubular member to position said distal end of said inner tubular member adjacent said distal end of said outer tubular member and said cutting edge adjacent said opening to permit said cutting edge to engage bodily tissue through said opening; and
    coating means formed on and secured to said inner tubular member and said cutting edge for forming an elongate bearing surface along the length of said inner tubular member, said inner tubular member having an outer diameter substantially the same as the inner diameter of said outer tubular member such that the clearance between the outer diameter of said outer tubular member and the inner diameter of said outer tubular member is approximately 0.0075 inches or less.

12. A surgical cutting instrument as recited in claim 11 wherein said coating means has a thickness of substantially 0.0001 inch.

13. A surgical cutting instrument as recited in claim 12 wherein said outer tubular member and said inner tubular member are each made of stainless steel.

14. A surgical cutting instrument as recited in claim 13 wherein said outer tubular member includes a proximal end with a plastic hub fixed thereto and said inner tubular member includes a proximal end with a plastic hub fixed thereto and having a portion received in said hub of said outer tubular member and a portion having a passage extending therethrough in communication with the lumen of said inner tubular member for aspiration of cut bodily tissue.

15. A surgical cutting instrument as recited in claim 11 wherein said elongate bearing surface of said inner tubular member has a surface hardness of approximately 80 Rc and greater.

16. A surgical cutting instrument as recited in claim 11 wherein said elongate bearing surface of said inner tubular member has a coefficient of friction of approximately 0.5 or less.

17. A surgical cutting instrument as recited in claim 11 wherein said inner tubular member is rotatably received in said outer tubular member.

18. A surgical cutting instrument as recited in claim 17 wherein said outer tubular member and said inner tubular member are each made of stainless steel and said outer tubular member includes a proximal end with a plastic hub fixed thereto and said inner tubular member includes a proximal end with a plastic hub fixed thereto over said coating and having a portion received in said hub of said outer tubular member and a portion having a passage extending therethrough in communication with the lumen of said inner tubular member for aspiration of cut bodily tissue.

19. A surgical cutting instrument as recited in claim 11 wherein said cutting edge is disposed below the longitudinal center line of said inner tubular member.

20. A surgical cutting instrument as recited in claim 19 wherein said cutting edge defines an acute angle at the outer diameter of said inner tubular member.

21. A surgical cutting instrument as recited in claim 11 wherein said coating means is formed on and secured to said inner tubular member by physical vapor deposition.

22. A surgical cutting instrument comprising
an elongate outer tubular member having a distal end and an opening disposed at said distal end;
an elongate inner tubular member having a distal end and a cutting edge disposed at said distal end, said inner tubular member being movably received in said outer tubular member to position said distal end of said inner tubular member adjacent said distal end of said outer tubular member and said cutting edge adjacent said opening to permit said cutting edge to engage bodily tissue through said opening; and
coating means formed on and secured to said inner tubular member by physical vapor deposition for forming an elongate bearing surface extending from said distal end to said proximal end of said inner tubular member, said inner tubular member having an outer diameter substantially the same as the inner diameter of said outer tubular member.

23. A surgical cutting instrument as recited in claim 22 wherein said coating means has a thickness of substantially 0.0001 inch.

24. A surgical cutting instrument as recited in claim 23 wherein said outer tubular member and said inner tubular member are each made of stainless steel.

25. A surgical cutting instrument as recited in claim 22 wherein said inner tubular member is rotatably received in said outer tubular member.

26. A surgical cutting instrument as recited in claim 25 wherein said outer tubular member and said inner tubular member are each made of stainless steel and said outer tubular member includes a proximal end and a plastic hub fixed thereto and said inner tubular member includes a proximal end and a plastic hub fixed thereto over said coating and having a portion received in said hub of said outer tubular member and a portion having a passage extending therethrough in communication with the lumen of said inner tubular member for aspiration of cut bodily tissue.

* * * * *

UNITED STATES PATENT AND TRADEMARK OFFICE
CERTIFICATE OF CORRECTION

PATENT NO. : 5,061,238
DATED : October 29, 1991
INVENTOR(S) : Donald K. Shuler

It is certified that error appears in the above-identified patent and that said Letters Patent is hereby corrected as shown below:

Column 6, line 7, after "a", insert --thickness of only--.

Signed and Sealed this

Twenty-fifth Day of May, 1993

Attest:

MICHAEL K. KIRK

*Attesting Officer*     *Acting Commissioner of Patents and Trademarks*